United States Patent [19]

Sommers

[11] Patent Number: 5,581,003
[45] Date of Patent: Dec. 3, 1996

[54] METHOD FOR MAKING SOLUBLE ZIRCONIUM AND HAFNIUM ORGANIC ACID COMPLEXES

[75] Inventor: James A. Sommers, Albany, Oreg.

[73] Assignee: Teledyne Industries, Inc., Albany, Oreg.

[21] Appl. No.: 473,961

[22] Filed: Jun. 7, 1995

[51] Int. Cl.$^6$ ........................... C07F 7/00
[52] U.S. Cl. ................................ 556/55
[58] Field of Search ...................... 556/55

[56] References Cited

U.S. PATENT DOCUMENTS

| 5,182,408 | 1/1993 | Sharif | 556/55 |
| 5,220,045 | 6/1993 | Knauf et al. | 556/55 |

FOREIGN PATENT DOCUMENTS

| 0781450 | 8/1957 | United Kingdom . |
| 0942741 | 11/1963 | United Kingdom . |

OTHER PUBLICATIONS

Warren B. Blumenthal, "The Chemical Behavior of Zirconium", D. Van Nostrand Co., Inc., Princeton, NJ, 1958, pp. 314–319.

R. C. Mehrotra & R. Bohra, "Metal Carboxylates", Academic Press, 1983, p. 240.

*Primary Examiner*—Porfirio Nazario-Gonzales
*Attorney, Agent, or Firm*—Shoemaker and Mattare, Ltd.

[57] ABSTRACT

Soluble zirconium and hafnium organic acid complexes are made by forming an aqueous mixture of a basic carbonate of either zirconium or hafnium and the organic acid such a propionic acid. The molar ratio of the organic acid to metal in the carbonate is greater than about 1.5. The mixture is heated with stirring to form the complex which is then recovered as a dry, free-flowing powder.

15 Claims, 1 Drawing Sheet

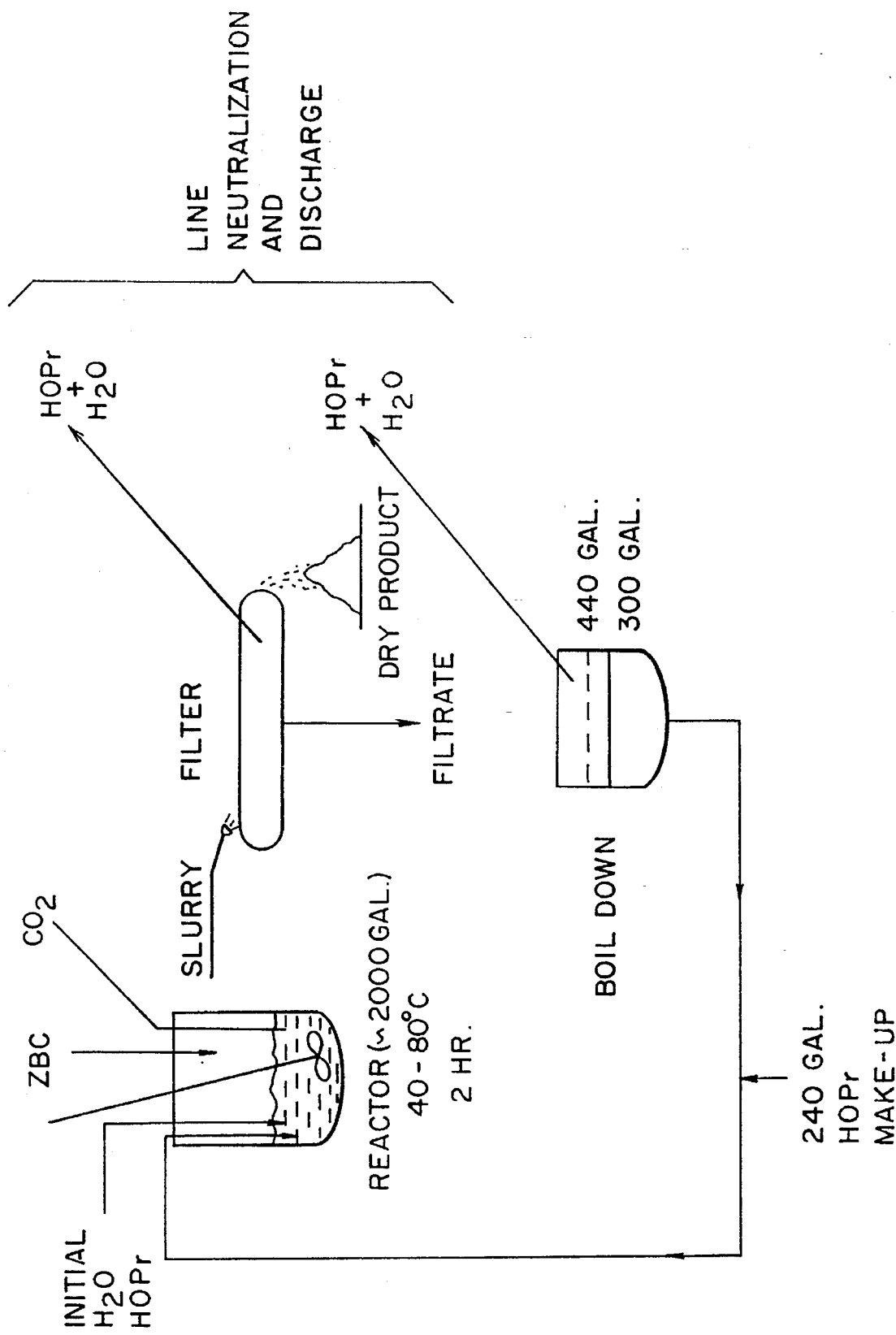

METHOD FOR MAKING SOLUBLE ZIRCONIUM AND HAFNIUM ORGANIC ACID COMPLEXES

BACKGROUND OF THE INVENTION

1. Field of the Invention

This invention relates to a method for making soluble zirconium and hafnium organic acid complexes.

2. Description of the Previously Published Art

Complexes of zirconium and hafnium with organic acids have several practical applications in industry. The most prominent one are related to the ability of these metal ions to serve as cross-linking agents for certain kinds of organic polymers which are used, for example, in the manufacture of paper. These applications require the complex containing the metal ion to be soluble in such media as alcohols. For several reasons it is desired that the complexes be obtainable as dry, free-flowing powders. This desire arises from economic and convenience criteria. It is usually undesirable to ship large volumes of a low-cost liquid over long distances. Furthermore, in using such chemicals, dry free-flowing powders are highly desirable for ease of transport and mixing.

Propionic acid complexes of zirconium are known and commercially available such as Magnesium Elektron's Z-plex (TM) 9700. However, reactions intended to prepare complexes from commercial starting materials often produce unsatisfactory products, i.e, ones which do not pass the solubility tests. A typical solubility test includes dissolving at least 65 g in 100 ml of isopropanol and at least 150 g in 100 ml of ethanol. Authoritative literature, however, fails to explain either the means or the reaction mechanisms for achieving products which pass such tests.

For example Blumenthal in "The Chemical Behavior of Zirconium" Van Nostrand, Princeton 1958, discuses formation of zirconium acetate complexes in detail, but on page 317 comments that compounds of other short-chained alkyl carboxylic acids have been studied only superficially. Blumenthal states that while carbonated hydrous zirconia is dissolved by formic acid and acetic acid, it is not dissolved by propionic acid. This statement by Blumenthal shows that this area is poorly understood since it has been discovered that zirconium basic carbonate does dissolve in an excess propionic acid.

In the book "Metal Carboxylates" Academic Press, London 1983, Mehrotra and Bohra discuss the behavior of zirconium acetates, but not synthesis of propionates. Page 240 incorrectly refers to a $MO(O_2CC_2H_5)_2 \cdot H_2O$ compound, but this is really about butyrates made by a different and commercially insignificant route.

3. Objects of the Invention

It is an object of this invention to provide a process for making organic acid complexes of zirconium and hafnium which are obtainable as dry powders and which are rapidly and readily soluble in alcohols.

It is a further object of this invention to provide a process for making propionic acid complexes of zirconium and hafnium which are obtainable as dry powders and which are rapidly and readily soluble in alcohols.

It is a further object of this invention to derive such complexes from inexpensive and commercially available precursors.

It is a further object of this invention to produce a process wherein high efficiencies of conversion to product of the zirconium and hafnium and also of the propionic acid are achieved.

It is a further object of this invention to provide a process which has a minimal impact on the environment by discharging a minimum amount of pollutants to the air and water.

These and further objects of the invention will become apparent from the following description of the invention.

SUMMARY OF THE INVENTION

Alcohol-soluble organic acid zirconium and hafnium complexes can be made by reaction of the respective carbonates with organic acids in certain preferred ranges of temperature, organic acid concentrations and molar ratio of the organic acid/metal. More particularly, by using propionic acid as a preferred acid, a propionic acid complex of zirconium and hafnium is obtained as a dry powder which is rapidly and readily soluble in alcohols. Outside these preferred ranges, one can obtain products which have many similar physical and chemical properties, but which may fail the solubility tests or which fail to even produce a solid product. Thus the preferred process of this invention as described in the examples utilizes critical parameters and preferred ranges to provide a novel process for producing these alcohol-soluble organic acid zirconium and hafnium complexes and especially producing propionic acid zirconium and hafnium complexes

BRIEF DESCRIPTION OF THE DRAWING

FIG. 1 illustrates a flow diagram for the process.

DESCRIPTION OF THE PREFERRED EMBODIMENTS

Alcohol-soluble organic acid zirconium and hafnium complexes are made by reaction of zirconium and hafnium basic carbonates with organic acids. The carbonates are commercially available and sources include Teledyne Wah Chang Albany in Albany, Oregon. As described in the Kirk-Othmer: Encyclopedia of Chemical Technology, v. 24, 3rd edition, 1984 basic zirconium carbonate is produced in a two-step process in which zirconium is precipitated as a basic sulfate from an oxychloride solution. The carbonate is formed by an exchange reaction between a water slurry of basic zirconium sulfate and sodium carbonate or ammonium carbonate at 80° C.

The organic acids used can be alkyl organic acids having up to about ten carbon atoms. The preferred acid is propionic acid.

The reaction between the basic carbonate and the organic acid is preferably conducted at a temperature of about 30°–90° C. and more preferably at about 40°–80° C.

It is also preferable to have the organic acid present in the aqueous phase, but not dilute enough to deleteriously reduce the solubility of the complexes formed in alcohol. The acid content of the acid and water mixture should be at least about 25% by weight.

When conducting the reaction the relative amounts of the metal basic carbonate and the acid should be controlled to insure the desired results. The amount of the acid present should be at least 1.5 times the molar amount of the metal present in the metal basic carbonate. Optimum ranges are where the molar acid/metal ratio is between about 1.5 and 3.0. From our experimental work we have found that if the mixture remains clear but becomes very viscous and gels completely before the requisite amount of the metal basic carbonate is mixed, then the resultant product will probably not meet the solubility specifications. However, if the requisite amount has been added and it remains clear, and if it becomes progressively more viscous as more material is added until you can't distribute the new solids any more, then you have been successful.

The following description of the preferred method of carrying out the process can be see with reference to the block flow diagram in the figure. The process is carried out by first heating in reactor 10 a mixture of the organic acid from supply 20 which is added by initial supply line 22 and initial water from water supply line 24 to a temperature of at least 30° C. The zirconium basic carbonate (ZBC) or hafnium basic carbonate (HBC) is added from supply container 26 slowly and the mixture is continuously stirred in the reactor. As the reaction proceeds carbon dioxide from the basic carbonate effervesces away. The reaction should be conducted until all of the carbon dioxide is gone and for a suitably long interval thereafter such as from about ½ hr to about 5 hr. When the reaction is complete, the solids formed in the aqueous mixture can be separated from the liquid. A preferred way to do this is to transfer the contents of the reactor 10 to a filter 30. The solids collected can be dried to achieve a dry, free-flowing powder in container 32. The filtrate can be recycled.

A preferred method to reuse the filtrate is to concentrate the filtrate in a concentrator 34 to relieve it of the imported water content from the basic carbonate. This can be done by boiling the filtrate in the concentrator 34. The concentrated filtrate can then have additional organic acid added via make up line 38 from the acid supply container 20 and the resultant mixture can be used as the starting mixture for the next production cycle.

A further environmental advantage of this system is the containment and neutralization of the effluents. The only non-recycled effluent are those formed during the filtering steps and the filtrate concentrating steps. The vapors from these two operations can be collected and neutralized with lime so that no acids are released into in the environment.

Having described the basic aspects of the invention, the following examples are given to illustrate specific embodiments thereof.

In these examples the starting material is commercial zirconium carbonate (nominally 40% $MO_2$), also known as zirconium basic carbonate (ZBC) and propionic acid (neat, b. p. 140°–142° C.), abbreviated as HOPr. The solubility test used is the dissolution of dried solid product in isopropanol to the extent of at least 6.5 g in 10 ml of isopropanol.

EXAMPLE 1

This example illustrates the production of zirconium propionic acid complex according to the present invention.

A mixture of 29 ml HOPr and 21 ml of water was heated to 46C and 50 g of ZBC was added. The molar ratio of HOPr/Zr was 2.4. The temperature dropped to 36° C. and the mixture was heated to 41° C. and held there for 1.5 hours. This mixture was readily stirrable. It was filtered and dried. The recovered product weighted 40.27 g and it passed the alcohol solubility test. The product was found by ignition to have a $MO_2$ content of 49%. The yield on Zr in this example was over 99%

EXAMPLE 2

This is a comparison example to illustrate an unsatisfactory production of zirconium propionic acid complex at room temperature.

To 50 g of ZBC was added 50 ml HOPr. The molar ratio of HOPr/Zr was 4.15. The mixture quickly became thick and unstirrable. Water was added in 5 ml increments until 25 ml had been added and the mixture could be magnetically stirred. The mixture effervesced throughout this procedure. The reaction appeared to be over in about 15 minutes. The mixture was vacuum filtered and dried. It failed the solubility test.

EXAMPLE 3

This is a comparison example to show the unsatisfactory effect of using a solution of HOPr which is too dilute at room temperature.

To 50 g of ZBC was added 100 ml water. Then 29.5 ml of HOPr was added over a period of about 10 minutes. The amount of acid in the acid and water mixture was about 22.8 wt. %. The product was collected and evaluated with the solubility test. In this test, for every 100 ml of isopropanol solvent the test requires at least 65 g of the powder to be dissolved into the solvent. However, when only about ⅓ of the amount corresponding to 65 g of powder was added, the mixture gelled completely to a clear gel state. This product powder did not meet the solubility test criteria.

EXAMPLE 4

This is a comparison example to show the unsatisfactory effect when the molar ratio of HOPr/Zr is too low even at an elevated temperature.

In Example 1 the molar ratio of HOPr/Zr was 2.4 and the product passed the solubility test. In this comparison example a mixture of 18 ml of HOPr and 21 ml of water were used with the addition of 50 g ZBC. This reaction mixture had a molar ratio of HOPr/Zr of only 1.5 and a within range amount of HOPr in the aqueous liquid phase of 46.2%. The same procedure was followed as in Example 1. The reaction product gelled extensively and did not pass the solubility test.

EXAMPLE 5

This example further delineates the relationship between of dilution and reaction temperature.

In a first experiment, Run A, 240 ml of HOPr and 600 ml water were mixed and heated to 45° C. Then 500 g of ZBC was added and the reaction was carried out as in Example 1. The molar ratio of HOPr/Zr was 2.0. The amount of acid in the aqueous solution was 28.6 wt. %. The resulting material did not pass the solubility test.

In a second experiment, Run B, the reaction was conducted in the same way, but the mixture was heated to 80° C. This product passed the solubility test, although it was very slow to dissolve. Thus, higher temperatures to some degree can overcome the effects of dilution. This example illustrates that if the mixture is too dilute and/or too cold, it may not work even if HOPr/Zr ratio is good and above a value of 1.5.

EXAMPLE 6

This example illustrates the process conducted in a cyclic manner to insure maximum efficiency for the conversion of the starting materials.

A mixture of 240 ml HOPr and 210 ml of water was heated to 45° C., and 500 g ZBC was stirred into the mixture. The mixture was continuously stirred and the temperature maintained at 45° C. for two hours, at which time it was filtered and 420 g of dried product was collected. The filtrate volume of 364 ml contained 10 wt % HOPr. One-half (180 ml) of this filtrate was used in a recycle batch as follows. The 180 ml portion was boiled down to 125 ml on a hot plate. Then, 100 ml of HOPr was added and the mixture heated to 45° C., at which time 250 g of ZBC was added to obtain a new half-batch of product as before. The amount of acid in the aqueous solution was 52 wt %. The dried product weighed 196 g and it passed the solubility test. The filtrate generated was 192 ml. This demonstrates the ability of the process to be conducted in a cyclic manner.

EXAMPLE 7

This example illustrates a further scale up of the process towards a commercial size.

A mixture of 2,400 ml HOPr and 400 ml water was heated to 80° C. in a stirred stainless steel tank. ZBC in an amount of 10 lb (4,540 g) was added to the mixture over 30 minutes. After 2 hours, the product was filtered on a 24 inch diameter table-top Buchner funnel. The filtrate volume was 5,450 ml and the dried product weighed 8.1 lb. The product passed solubility tests for both isopropanol and for ethanol where a solubility of greater than 150 g per 100 ml of ethanol was achieved. This represents a ten-fold scaleup over the previous batch size, which itself was a ten-fold scaleup from the initial experiment.

EXAMPLE 8

This example illustrates a larger scale production of the product with recycle.

A mixture was made of 5,000 pounds of ZBC having 40% $MO_2$ content with 290 gallons of HOPr (2,400 lb) and 250 gallons of water. The reactants were stirred and heated at 60° C. for 2 hours. The dry product obtained was 4,000 lb which had a solubility in isopropyl alcohol of greater than or equal to 6.5 g/10 ml. The filtrate was 440 gallons which was boiled down to 300 gallons. This was recycled back to the reactor where 240 gallons of fresh HOPr was added to form a second batch to which was added 5,000 lb of ZBC and the process was continued. During the first process the HOPr emissions amounted to 80 lb from the reactor and 40 lb from the boil down for a total of 120 lb of HOPr which was neutralized with 60 lb of lime.

It is understood that the foregoing detailed description is given merely by way of illustration and that many variations may be made therein without departing from the spirit of this invention.

What is claimed is:

1. A process for making a solid complex of either zirconium or hafnium with an organic acid where the complex is highly soluble in alcohols comprising the steps:

a) forming an aqueous mixture of
   a) a basic carbonate of a metal selected from the group consisting of zirconium, hafnium and mixtures thereof, and
   b) an organic acid, such that the molar ratio of organic acid to metal in the carbonate is greater than about 1.5;

b) heating the aqueous mixture with mixing to form the complex; and c) recovering the complex as a dry, free-flowing powder.

2. A process according to claim 1, wherein the heating in step (b) is continued for a sufficient period of time after substantially all the carbon dioxide of the parent basic carbonate has effervesced away to insure substantial completion of the reaction.

3. A process according to claim 1, wherein the recovery of the solid complex from the mixture in step (c) includes:

a) separating the liquid from the solids formed; and b) drying the solids to achieve a dry, free-flowing powder.

4. A process according to claim 1, wherein the reaction temperature is maintained at about 30°–90° C.

5. A process according to claim 4, wherein the reaction temperature is about 40°–80° C.

6. A process according to claim 1, wherein the water and acid mixture of step (a) has an acid content of at least 25 wt %.

7. A process according to claim 1, wherein the molar acid/metal ratio is between about 1.5 and 3.0.

8. A process according to claim 1, wherein the organic acid has 1–10 carbon atoms.

9. A process according to claim 1, wherein the organic acid is propionic acid.

10. A process according to claim 1, wherein the complex is soluble in isopropanol to the extent of at least 6.5 g per 10 ml of isopropanol.

11. A process according to claim 1, wherein the complex is soluble in ethanol to the extent of at least 150 g per 100 ml of ethanol.

12. A process according to claim 1, further comprising:

a) recovering the filtrate remaining after the complex is recovered in step (c);

b) concentrating the filtrate to relieve it of the imported water content from the basic carbonate; and c) adding make up organic acid so as to form the starting mixture for step (a) for the next production cycle.

13. A solid complex of either zirconium or hafnium and an organic acid having 1–10 carbon atoms made by the process of claim 1 and having a high solubility in alcohol.

14. A solid complex according to claim 13, wherein the complex is soluble in isopropanol to the extent of at least 6.5 g per 10 ml of isopropanol.

15. A solid complex according to claim 13, wherein the complex is soluble in ethanol to the extent of at least 150 g per 100 ml of ethanol.

* * * * *